United States Patent [19]
Rössiger et al.

[11] Patent Number: 6,038,280
[45] Date of Patent: Mar. 14, 2000

[54] METHOD AND APPARATUS FOR MEASURING THE THICKNESSES OF THIN LAYERS BY MEANS OF X-RAY FLUORESCENCE

[75] Inventors: Volker Rössiger, Sindelfingen; Karl-Heinz Kaiser, Böblingen, both of Germany

[73] Assignee: Helmut Fischer GmbH & Co. Institut Fur Electronik Und Messtechnik, Sindelfingen, Germany

[21] Appl. No.: 09/038,820

[22] Filed: Mar. 12, 1998

[30] Foreign Application Priority Data

Mar. 13, 1997 [DE] Germany ............................ 197 10 420

[51] Int. Cl.[7] .................................................. G01B 15/02
[52] U.S. Cl. ................................................ 378/50; 378/44
[58] Field of Search ......................................... 378/50, 44

[56] References Cited

U.S. PATENT DOCUMENTS

| | | | |
|---|---|---|---|
| 4,534,049 | 8/1985 | Koga | 378/50 |
| 4,597,093 | 6/1986 | Fischer | 378/44 |
| 5,299,252 | 3/1994 | Takahashi | 378/50 |

FOREIGN PATENT DOCUMENTS

| | | |
|---|---|---|
| 0325158 | 7/1989 | European Pat. Off. . |
| 59068608 | 4/1984 | Japan . |

Primary Examiner—Craig E. Church
Attorney, Agent, or Firm—Antonelli, Terry, Stout & Kraus, LLP

[57] ABSTRACT

The invention relates to a method for measuring the thicknesses of thin layers by X-ray fluorescence, in which a specimen having the layer to be studied is positioned in view and subsequently X-radiation is directed onto the layer to be studied and emitted fluorescent radiation is detected by means of a radiation detector and the layer thickness is determined, in which on positioning the specimen there is a focussing by adjusting a focussing element along its optical axis and the position of the focussing element is determined with the layer in focus. An apparatus for layer thickness measurement with X-ray fluorescence according to the invention having a X-ray tube, a detector and an observing device with a focussing element provides for the latter to be movably mounted along its optical axis and provided with a position measuring device. This obviates the need for having to move a workpiece-carrying table in such a way that the work surface comes to rest at a predetermined, specific measuring distance or spacing.

13 Claims, 2 Drawing Sheets

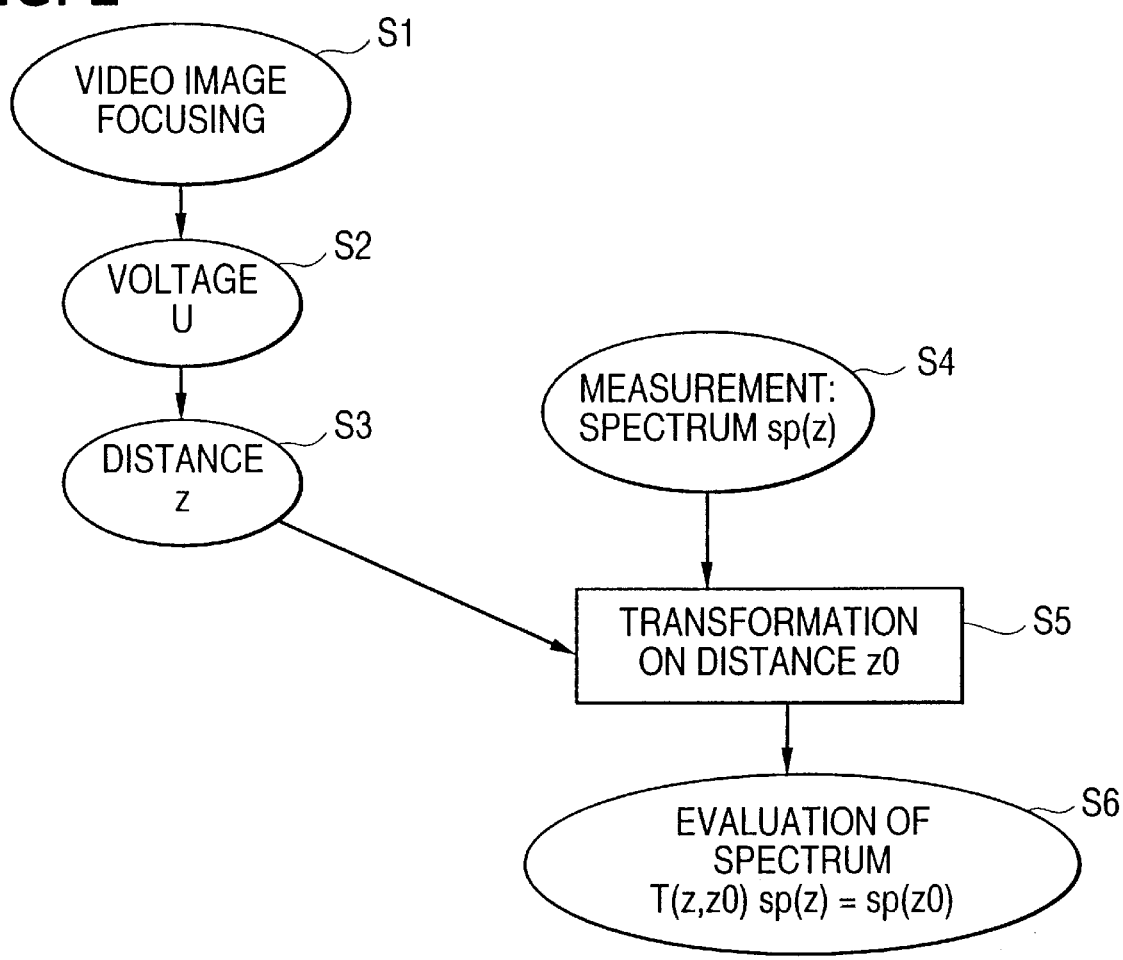

METHOD AND APPARATUS FOR MEASURING THE THICKNESSES OF THIN LAYERS BY MEANS OF X-RAY FLUORESCENCE

BACKGROUND OF THE INVENTION

1. Field of the Invention

The invention relates to a method for measuring thicknesses of thin layers by means of X-ray fluorescence, in which a specimen having the layer to be studied is positioned in view and subsequently X-radiation is directed onto the layer being studied and emitted fluorescent radiation is detected by means of a detector and the layer thickness determined, as well as an apparatus for layer thickness is measured by X-ray fluorescence using an X-ray tube, a detector and an observing device with a focussing element.

Such methods and apparatuses are used for measuring the thickness and also the composition of X-ray fluorescence-producing layers, particularly galvanic layers in the micrometer range. The composition of alloy layers can also be determined.

2. Description of the Prior Art

In the case of the known apparatuses and methods, it is necessary for the surface of the workpiece to have a fixed distance from the detector and the X-ray source (both being fixed together). If it is necessary to study workpieces having different heights or thicknesses, then the distance between the specimen table and the detector or radiation source must be modified, so that the work surface facing the radiation source and the detector always has a constant distance from the radiation source. This can be brought about in that the workpiece-carrying specimen table or the measuring head containing the detector and radiation source is measured in the Z-direction, i.e. towards the X-radiation. The nominal distance is checked with optical means. This e.g. takes place in that the measuring head or specimen table are moved until the work surface is in the focus of a camera, i.e. is seen in focus by an optics.

Apparatuses for measuring the thickness by X-ray fluorescence are also known, which are able to operate with several fixed measurement distances. For specific applications shorter measurement distances are desired, because the measurement sensitivity for thinner layers is then better and in the case of a fixed collimator there is a smaller measuring spot due to the divergence of the primary X-ray bundle. With longer measurement distances the measurement sensitivity for thicker layers is better and in addition it is possible to measure depressions in the work surface or coating.

The tracing or tracking of a measuring head and specimen table involves a high mechanical cost and effort, because it is necessary to have a precise movement and positioning of a weight of a few kg. Thus, movement can also only take place slowly, so that it requires a considerable time, which is comparable to or longer than the measuring time.

Therefore the problem solved by the invention is to provide a method and an apparatus, in which the constructional expenditure for the precise movement of a specimen table or measuring head is obviated and there is no need for a time-consuming positioning of the work carrier or measuring head.

SUMMARY OF THE INVENTION

According to the invention the problem of the prior art is solved in the case of a method of the aforementioned type in that on positioning the specimen a focussing takes place through adjusting a focussing element along its optical axis and the position of the focussing element is determined with the layer in focus. An apparatus solution to the aforementioned problem provides for the focussing element being movably mounted along its optical axis and being provided with a position measuring device.

As a result of the invention, a workpiece or the coating of its surface can be analyzed at a random distance from the measuring head, because a focussing is merely brought about by moving a focussing element, such as in particular a lens, which can be moved much more rapidly, because it only has a limited weight. In addition, the position of the focussing element is determined when focussing has taken place, so that it is possible to establish the distance of the work surface from the detector or X-ray apparatus and consequently a measurement can be performed with a random distance or spacing.

According to a preferred development of the invention the position of the focussing element is electrically determined. For this purpose a potentio-meter, preferably a rotary potentiometer can be provided, which is connected to a rotary head, with which the linear position of the focussing element in the direction of its optical axis can be adjusted, e.g. by means of a toothed belt drive or a spindle. According to another preferred development of the method, the focussing takes place automatically. The apparatus according to the invention uses an autofocussing device for the observing device. Focussing can take place in different ways. According to a preferred development the focussing element is moved into a position, in which the surface of the workpiece reveals a maximum contrast in an image produced by the focussing element.

According to a further development of the invention, a correction of the actual layer thickness measurement whilst using the focussing element position determined by means of the position measuring device takes place. In specific form this can take place in that the correction of the layer thickness measurement is carried out by a transformation $T(z,z0)$ of the fluorescent radiation spectrum $sp(z)$ obtained with the actual measurement distance z of the layer from the detector on a spectrum $sp(z0)$ for a desired measurement distance z0 corresponding to $$sp(z0)=T(z,z0)\ sp(z)$$

From the apparatus standpoint, the invention provides a device for correcting the layer thickness measurement by means of the focussing device position measured by the focussing device, the correcting device having a device for the transformation $T(z,z0)$ of the spectrum $sp(z)$ obtained at the actual measurement distance of the layer from the detector on a measured result $sp(z0)$ for a desired measurement distance z0 corresponding to $$sp(z0)=T(z,z0)\ sp(z)$$

The desired or predetermined measurement distance z0 can be that at which the apparatus was calibrated. The measured result $sp(z)$ designates the fluorescence spectrum measured in the actual distance z and is e.g. a vector with 256 components, which corresponds to the pulse height distribution and consequently the energy distribution of a proportional counter tube detector. The measuremed result $sp(z0)$ is then the spectrum for the distance at which the apparatus was calibrated. $T(z,z0)$ is the transformation operator, which converts the spectrum $sp(z)$, measured in the distance z, as if it was measured in the desired distance z0.

The invention more particularly makes it possible to measure X-ray fluoresceable layers at a random distance, without a fluorescence intensity of the fundamental material of the workpiece being measurable, because e.g. the top layers excessively absorb such a fluorescence or if the fundamental material emits no measurable fluorescent radiation.

BRIEF DESCRIPTION OF THE DRAWINGS

Further advantages and features of the invention can be gathered from the claims and the following description of an embodiment of the invention with reference to the attached drawings, wherein show:

FIG. 2 is a flow chart of the inventive method.

DETAILED DESCRIPTION OF THE PREFERRED EMBODIMENTS

Figure 1:
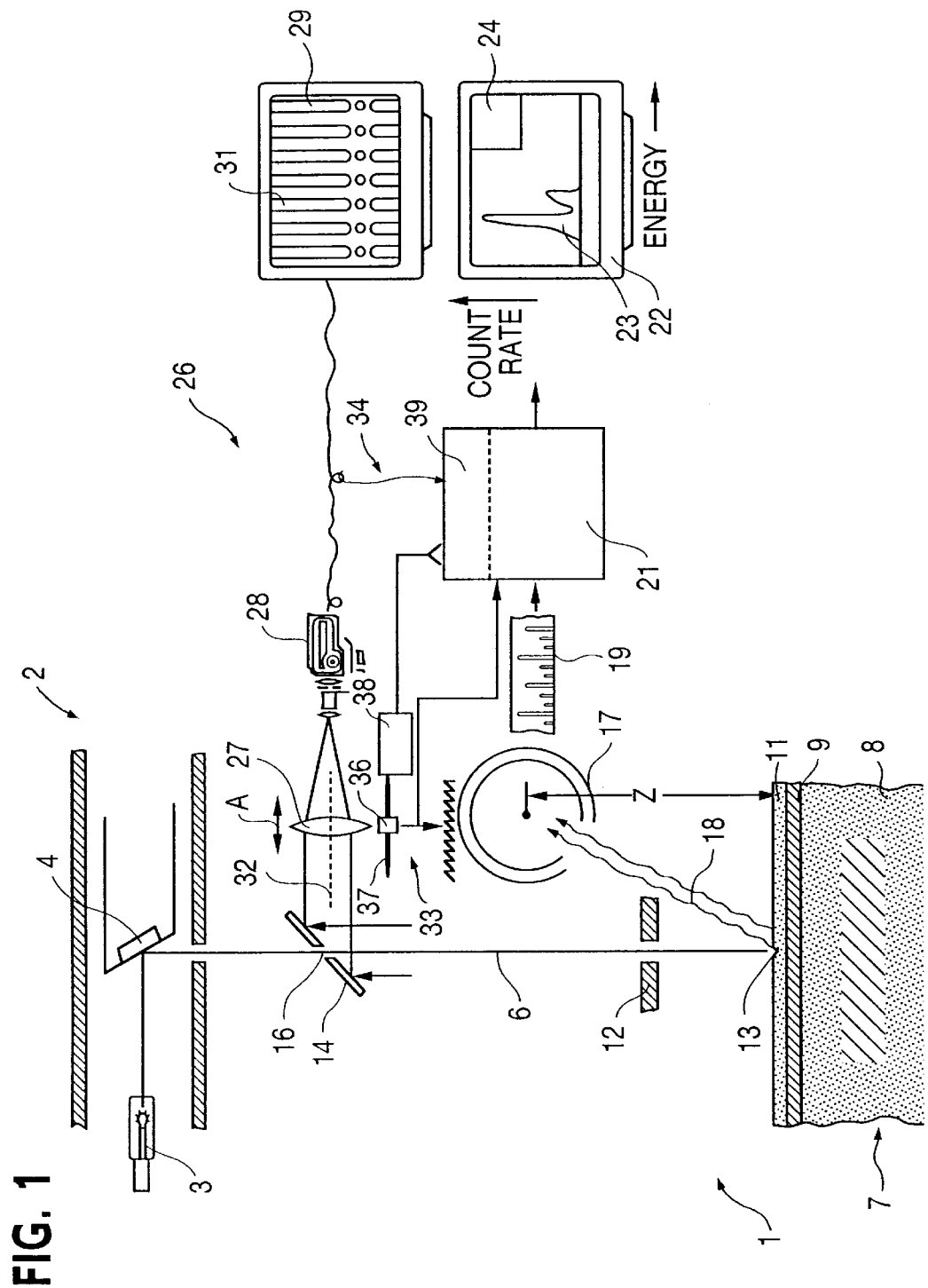
FIG. 1 is a diagrammatic construction of the inventive apparatus.

The apparatus 1 according to the invention for measuring thin layers by X-ray fluorescence has a X-ray tube 2 with a cathode 3 and an anode 4, from which an X-ray 6 is directed onto the object 7 being studied and which, on a fundamental material 8, in the represented embodiment has two top layers 9, 11 made from different materials.

Between the X-ray tube 2 and workpiece 7 is provided a collimator with which a narrow range can be blocked out of the X-ray 6, so as in this way to produce a closely defined X-ray spot 13 on and in the workpiece 7, including its two layers 9, 11.

Between the X-ray tube 2 and collimator 12 is also provided a reflecting mirror 14, which has an orifice 16 through which passes the X-ray 6. The impact point 13 of the X-ray 6 can be observed by means of the reflecting mirror 14.

The apparatus also has a detector 17, which is constructed as a potential counter tube and which receives the fluorescent radiation 18 produced through the X-ray 6 in the layers 9, 11 and, in the case of thin layers, also in the fundamental material 8 and, corresponding to the energy of the radiation, emits pulse-shaped signals 19, whose height is proportional to the energy of a fluorescence quantum. The signals 19 are processed in an evaluating unit 21 and can be represented on a screen 22, e.g. as a pulse height distribution 23. Additionally in a partial window 24 of the screen 22 are shown the measured thicknesses of the layers 9, 11 and can be emitted by means of a connected printer.

In order to ensure that the area of the workpiece 7 to be studied is correctly positioned in the X-ray 6, an optical observing device 26 is provided, which has in addition to the aforementioned reflecting mirror 14 a focussing element 27 in the form of a lens, a camera 28 and a reproduction screen 29, which can be identical to the screen 22. The optical image 31 of the work surface, represented in the embodiment on the screen 29, and the pulse height distribution can be reproduced in corresponding windows of the single screen.

By means of the known observing device which, in place of the camera 28 and screen 29, can also incorporate an eyepiece for the direct observation of the impact spot 13, the workpiece can be so oriented that its area to be studied is precisely located in the X-ray 6.

In the inventive apparatus shown, the focussing element 27 is displaceably arranged in the direction of its optical axis 32, as indicated by the arrow A. It can e.g. be manually moved along a guide. In addition, to the focussing element 27 is connected a position measuring device 33 for establishing the position of the focussing element 27 along the optical axis 32 and which in the represented embodiment is constructed as a potentiometer. In general, it is a rotary potentiometer on a corresponding adjusting device. In the represented embodiment the position of the focussing element 27 can be driven in motor manner and in particular automatically by an autofocussing device 34.

For this purpose the focussing element 27 is mounted by means of a threaded block 36 on a spindle 37, which is driven by a motor 38. The drive of the motor 38 is regulated by means of an autofocussing unit 39, which can be located within the evaluating unit 21, in that at different positions of the focussing element 27 the contrast of the image recorded by the camera 28 is determined and the focussing element is so adjusted by the described drive that maximum contrast is obtained. Such autofocussing devices are known per se, so that a detailed description thereof is unnecessary here.

The sequence of the inventive method according to FIG. 2 will now be given. Firstly in stage S1 there is a focussing, i.e. a focussing of the video image corresponding to $$1/f - 1/s1 + 1/(s21+s22),$$

in which s1 is the image distance, s21 the distance between the lens and the mirror, s22 the distance between the mirror and the work surface and consequently s21+s22 the distance of the lens from the work surface.

As stated, focussing can take place automatically or manually by means of a focussing handle or lever.

On carrying out a focussing, in a stage S2 the voltage value is established on a potentiometer, optionally a rotary potentiometer. The voltage value is represented by means of an analog-digital converter as a digital and consequently numerical value $U_{dig}$.

For further evaluation it is necessary to have the distance between the work surface and the detector 17, optionally as a projection between the work surface and center of the detector. This can be calculated according to stage S3 by means of an empirically determined or calibrated relationship $$z = f(U_{dig}).$$

Subsequently the fluorescence spectrum measurement is performed (stage S4). In a further stage S5 there is a transformation of the spectrum measured at distance z to a fixed distance z0, at which the system was calibrated, according to $$sp(z0) = T(z,z0) \, sp(z).$$

Thus, from the measured spectrum sp(z), measured at the distance z, the spectrum sp(z0) is determined, which corresponds to a measurement at the distance z0 at which calibration took place.

As roughly a specific energy E can be associated with each current pulse distribution value, the transformation law used as a basis for the operator T can be established from the response probability W of the proportional counter tube as a function of the radiant energy E and distance z.

The response probability W(E,z) is given by:
  the solid angle $\Omega$, under which an entrance window of the detector 17 is seen from the workpiece 7,
  the probability w air for the absorption within the air distance between specimen and detector window,
  the probability w window for the absorption within the detector window and
  the probability w gas for the absorption within the active volume of the counter tube.

All these quantities can easily be calculated from the absorption coefficients $\mu$ (tabulated), which are dependent on the energy E. Thus, the sought response probability is $$W(E,z)=(\Omega/4\pi)(1-w\ air)*(1-w\ window)*w\ gas.$$

For small energy intervals (E . . . E+d_E) the correction factor with which the associated partial intensity of the spectrum sp(z) in said range (E . . . E+d_E) must be multiplied is $$W(E,z0)/W(E,z).$$

After each partial interval of the spectrum has been multiplied by the correction factor relevant for the energy, the spectrum can be treated as if it was measured with a fixed distance z0. It is then possible to evaluate the spectrum in a conventional, known manner for determining the layer thickness (stage S6).

In an embodiment a 17 $\mu$m thick copper layer was investigated on a support material of ABS (acrylonitrile-butadiene-styrene copolymer). Calibration took place at a distance z0=89.3 mm. In addition to this distance z0, measurements were performed at distances z=79.3 mm and z=129.3 mm. The measured results with the inventive apparatus (for a measuring time of 10 sec) can be gathered from the following table:

| z (mm) | Measured result d Cu ($\mu$m) with height change correction |
|---|---|
| 79.3 | 17.8 +/− 0.4 |
| 89.3 | 17.0 +/− 0.4 |
| 129.3 | 17.8 +/− 0.6 |

We claim:

1. A method for measuring thickness of a layer by X-ray fluorescence comprising:

positioning a specimen having a layer to be studied in a view of an X-ray source;

directing x-rays from the x-ray source onto the layer being studied which causes fluorescent radiation to be emitted from the layer;

detecting the fluorescent radiation with a detector;

adjusting a focusing device along an optical axis to focus an image of the specimen;

determining a position of the focusing device when the image of the specimen is in focus; and producing a thickness measurement which is corrected in response to the fluorescent radiation detected by the detector and the determined position of the focusing element.

2. A method in accordance with claim 1 wherein:

the position of the focusing element is electrically determined.

3. A method in accordance with claim 1 wherein;

the adjusting of the focusing element along an optical axis to focus the image of the specimen is performed automatically.

4. A method in accordance with claim 2 wherein;

the adjusting of the focusing element along an optical axis to focus the image of the specimen is performed automatically.

5. A method in accordance with claim 3 wherein:

the adjusting of the focusing element produces a maximum contrast in the image produced by the focusing element.

6. A method in accordance with claim 4 wherein:

the adjusting of the focusing element produces a maximum contrast in the image produced by the focusing element.

7. A method in accordance with claim 1 wherein:

a camera and a screen displays the image produced by the focusing element.

8. A method in accordance with claim 1 wherein:

correction of the thickness measurement is performed by a transformation T(z,z0) of a measurement sp(z) obtained from an actually measured distance z of the layer from the detector to a measured result sp(z0) for a desired measurement distance z0 corresponding to sp(z0)=T(z,z0) sp(z).

9. An apparatus for measuring thickness of a layer of a specimen by X-ray fluorescence comprising:

an X-ray source providing X-rays for irradiating the specimen which causes flourescent radiation to be emitted from the layer;

a detector which detects the flourescent radiation emitted by the specimen;

a focusing device which is adjustable along an optical axis to focus an image of the specimen;

a position measuring device for measuring a position of the focusing element when the image of the specimen is in focus; and an evaluation unit for processing the position of the focusing element when the image is in focus and the radiation detected by the detector to produce a thickness measurement which is corrected.

10. An apparatus in accordance with claim 9 wherein:

the position measuring device is a potentiometer.

11. An apparatus in accordance with claim 9 further comprising:

a camera and screen which displays the image produced by the focusing element.

12. An apparatus in accordance with claim 9 wherein:

the focusing element is an autofocusing device.

13. An apparatus in accordance with claim 10 wherein:

the focusing element is an autofocusing device.

* * * * *